(12) United States Patent
Zhang (10) Patent No.: US 11,517,494 B2
(45) Date of Patent: Dec. 6, 2022

(54) THERMOSTATIC MASSAGE PAD (71) Applicant: Jianping Zhang, Beijing (CN)

(72) Inventor: Jianping Zhang, Beijing (CN)

(\*) Notice: Subject to any disclaimer, the term of this patent is extended or adjusted under 35 U.S.C. 154(b) by 728 days.

(21) Appl. No.: 16/578,435

(22) Filed: Sep. 23, 2019

(65) Prior Publication Data
US 2020/0375840 A1 Dec. 3, 2020

(30) Foreign Application Priority Data

May 31, 2019 (CN) .......................... 201910469837.3

(51) Int. Cl.
| | | |
|---|---|---|
| *A61H 9/00* | (2006.01) | |
| *A61F 7/00* | (2006.01) | |
| *A61H 23/02* | (2006.01) | |
| *A61G 7/057* | (2006.01) | |
| *F25B 21/02* | (2006.01) | |

(52) U.S. Cl.
CPC ........... *A61H 9/0078* (2013.01); *A61F 7/007* (2013.01); *A61F 7/0053* (2013.01); *A61H 23/0254* (2013.01); *A61F 2007/0057* (2013.01); *A61F 2007/0075* (2013.01); *A61F 2007/0086* (2013.01); *A61F 2007/0091* (2013.01); *A61F 2007/0096* (2013.01); *A61H 2201/0103* (2013.01); *A61H 2201/0207* (2013.01); *A61H 2201/0214* (2013.01); *A61H 2201/0242* (2013.01); *A61H 2201/0285* (2013.01); *A61H 2201/5053* (2013.01); *A61H 2201/5082* (2013.01); *F25B 21/02* (2013.01); *F25B 2321/02* (2013.01); *F25B 2321/021* (2013.01); *F25B 2321/0252* (2013.01)

(58) Field of Classification Search
CPC . A61H 9/0078; A61H 23/0254; A61F 7/0053; A61F 7/007
See application file for complete search history.

(56) References Cited

U.S. PATENT DOCUMENTS 6,139,512 A * 10/2000 Ricchio ................ A61H 9/0021
601/55
6,155,995 A * 12/2000 Lin ......................... A61F 7/007
601/79

(Continued)

FOREIGN PATENT DOCUMENTS

WO WO-2017207636 A1 * 12/2017 ............... A61F 7/00

*Primary Examiner* — Samchuan C Yao
*Assistant Examiner* — Minhua Zhao
(74) *Attorney, Agent, or Firm* — Bayramoglu Law Offices LLC (57) ABSTRACT

A thermostatic massage pad includes: a thermostatic pad, wherein a thermostatic water pipe is arranged inside the thermostatic pad; a cooling pad, wherein a cooling water pipe is arranged inside the cooling pad; a casing, wherein a thermostatic water pump and a cooling water pump are respectively arranged inside the casing, a thermostatic water tank is arranged at a top of the thermostatic water pump, a cooling water tank is arranged at a top of the cooling water pump, a water inlet end of the thermostatic water pump is connected to a water outlet of the thermostatic water tank, and a water inlet end of the cooling water pump is connected to a water outlet of the cooling water tank; a thermoelectric cooler, wherein an end surface of the thermoelectric cooler is fixedly connected to a wall surface of the thermostatic water tank.

10 Claims, 6 Drawing Sheets (56) References Cited

U.S. PATENT DOCUMENTS

| | | | | |
|---|---|---|---|---|
| 2004/0249427 | A1* | 12/2004 | Nabilsi | A61F 7/0085 |
| | | | | 607/104 |
| 2006/0053558 | A1* | 3/2006 | Ye | A47C 27/18 |
| | | | | 5/689 |
| 2012/0016274 | A1* | 1/2012 | Howe | A61M 21/02 |
| | | | | 601/148 |
| 2016/0302963 | A1* | 10/2016 | Yang | A61F 7/007 |
| 2019/0099288 | A1* | 4/2019 | Vergara | A61F 7/007 |

* cited by examiner

THERMOSTATIC MASSAGE PAD

CROSS REFERENCE TO THE RELATED APPLICATIONS

This application is based upon and claims priority to Chinese Patent Application No. 201910469837.3, filed on May 31, 2019, the entire contents of which are incorporated herein by reference.

TECHNICAL FIELD

The present disclosure belongs to the technical field of medical treatment and more specifically, relates to a thermostatic massage pad.

BACKGROUND

Pressure sores, also known as pressure ulcers and bedsores, usually develop in local tissues suffering from long-term compression, sustained tissue ischemia, hypoxia, and malnutrition. These tissues result in tissue ulceration and necrosis. Skin pressure sores are a common complication in rehabilitation therapy and nursing care. Due to poor heat dissipation in the contact area between the human body and the mattress, ulceration is developed in local body parts. Paralyzed patients having challenges in turning their body, patients after surgery and the like need a device that can promote local blood circulation at the part of the body under pressure and helps in heat dissipation.

SUMMARY

Therefore, the technical problem to be solved by the present disclosure is to overcome the problem of poor heat dissipation in the contact area between the body of a patient having challenges in turning their body and the mattress in the prior art.

For this purpose, the present disclosure employs the following technical solution. A thermostatic massage pad, including:

a thermostatic pad, wherein a thermostatic water pipe is arranged inside the thermostatic pad;

a cooling pad, wherein a cooling water pipe is arranged inside the cooling pad;

a casing, wherein a thermostatic water pump and a cooling water pump are respectively arranged inside the casing, a thermostatic water tank is arranged at the top of the thermostatic water pump, a cooling water tank is arranged at the top of the cooling water pump, a water inlet end of the thermostatic water pump is connected to a water outlet of the thermostatic water tank, and a water inlet end of the cooling water pump is connected to a water outlet of the cooling water tank;

a thermoelectric cooler, wherein an end surface of the thermoelectric cooler is fixedly connected to a wall surface of the thermostatic water tank, the other end surface of the thermoelectric cooler is fixedly connected to a wall surface of the cooling water tank;

a thermostatic connecting water pipe, wherein an end of the thermostatic connecting water pipe is connected to a water outlet end of the thermostatic water pump, the other end of the thermostatic connecting water pipe is connected to an end of the thermostatic water pipe, and the other end of the thermostatic water pipe is connected to a water inlet of the thermostatic water tank;

a cooling connecting water pipe, wherein an end of the cooling connecting water pipe is connected to a water outlet end of the cooling water pump, the other end of the cooling connecting water pipe is connected to an end of the cooling water pipe, and the other end of the cooling water pipe is connected to the water inlet of the cooling water tank;

a controller, wherein the controller is arranged on an inner wall of the casing, and the controller is electrically connected to the thermoelectric cooler; and a power supply, wherein the power supply is arranged on an inner wall of the casing and is electrically connected to the thermoelectric cooler, the thermostatic water pump, and the cooling water pump, respectively.

Preferably, the thermostatic massage pad further includes a massage device, and the massage device includes:

a massage pad, wherein a plurality of independent airbags are arranged in the massage pad;

inflation solenoid valves, wherein the inflation solenoid valves are arranged inside the casing and are electrically connected to the controller;

a plurality of air pipes, wherein the air pipes are connected to the airbags at an end, and the air pipes are connected to the outlet ends of the inflation solenoid valves at the other end;

a compressed air multi-way connector, wherein the compressed air multi-way connector is arranged inside the casing, a plurality of output ends of the compressed air multi-way connector are respectively connected to the inlet ends of the inflation solenoid valves;

a deflation solenoid valve, wherein the deflation solenoid valve is arranged inside the casing, an inlet of the deflation solenoid valve is connected to an air discharge port of the compressed air multi-way connector, an outlet of the deflation solenoid valve is connected to the outside, and the deflation solenoid valve is electrically connected to the controller; and an air pump, wherein the air pump is arranged inside the casing, and an output end of the air pump is connected to an air inlet port of the compressed air multi-way connector.

Preferably, a heating plate is arranged on the wall surface of the thermostatic water tank, and the heating plate is electrically connected to the controller.

Preferably, the thermostatic massage pad further includes:

a temperature sensor, wherein the temperature sensor is arranged on an inner wall of the thermostatic water tank, and the temperature sensor is electrically connected to the controller; and a control panel, wherein the control panel is arranged on an outer wall of the casing, and the control panel is electrically connected to the controller.

Preferably, the thermostatic water pipe includes a plurality of water pipe network modules. The plurality of water pipe network modules are arranged in a rectangular array manner in the thermostatic pad, and each water pipe network module includes:

a first water inlet pipe;

a first curved water pipe, wherein the first curved water pipe is curved along a counterclockwise direction, and an inlet end of the first curved water pipe is connected to an outlet end of the first water inlet pipe;

an S-shaped water pipe, wherein an inlet end of the S-shaped water pipe is connected to an outlet end of the first curved water pipe;

a second curved water pipe, wherein the second curved water pipe is curved along a clockwise direction in opposite to the first curved water pipe, an inlet end of the second curved water pipe is connected to an outlet end of the S-shaped water pipe, and the second curved water pipe is of an arc shape; and a first water outlet pipe, wherein an inlet end of the first water outlet pipe is connected to an outlet end of the second curved water pipe;

the plurality of water pipe network modules are successively connected end to end, and the inlet end of the first water inlet pipe of the first network module is connected to an end of the thermostatic connecting water pipe away from the thermostatic water pump, the outlet end of the first water outlet pipe of the last water pipe network module is connected to the water inlet of the thermostatic water tank.

Preferably, a cooling fan and a water-cooled radiator are installed on the cooling connecting water pipe. The cooling fan is arranged in parallel with the water-cooled radiator and the cooling fan is electrically connected to the controller.

The water-cooled radiator includes:

a water-cooled radiator housing, wherein the water-cooled radiator housing includes a plurality of connecting plates, the plurality of the connecting plates make an accommodating chamber, the water-cooled radiator housing has a water collecting area on a side with the accommodating chamber, one of the connecting plates is arranged with a water-cooled radiator water inlet and a water-cooled radiator water outlet, the water-cooled radiator water inlet and the water-cooled radiator water outlet are arranged in the water collecting area, and the water-cooled radiator water inlet and the water-cooled radiator water outlet are both connected to the accommodating chamber;

a heat exchange module, wherein the heat exchange module is arranged inside the accommodating chamber, and the heat exchange module includes a plurality of wavy cooling fins;

a second water inlet pipe, the second water inlet pipe is inserted in the water-cooled radiator water inlet, an end of the second water inlet pipe is exposed outside the water-cooled radiator housing and is connected to an inlet end of the cooling connecting water pipe, and the other end of the second water inlet pipe extends from the water-cooled radiator water inlet to the accommodating chamber;

a second water outlet pipe, wherein the second water outlet pipe is inserted in the water-cooled radiator water outlet, an end of the second water outlet pipe is exposed outside the water-cooled radiator housing and is connected to an output end of the cooling connecting water pipe, the other end of the second water outlet pipe extends from the water-cooled radiator water outlet to the accommodating chamber, the second water outlet pipe is provided with a water outlet side hole at the end extending into the accommodating chamber, and in the water-cooled radiator structure, the water outlet side hole is covered by the water in the accommodating chamber to prevent air from entering the second water outlet pipe and a partition plate, wherein the partition plate is arranged inside the accommodating chamber and is located between the second water inlet pipe and the second water outlet pipe, and the partition plate connects two opposite inner wall surfaces of the accommodating chamber.

Preferably, the air pipes are further provided with an airbag vibration device and the airbag vibration device includes:

a cylinder, arranged at a position near the air pipes;

a connecting pipe, wherein an end of the connecting pipe is connected to the air pipes, and the other end of the connecting pipe is connected to a left end of the cylinder;

a piston, wherein the piston is arranged inside the cylinder, and the piston reciprocates left and right within the cylinder;

a movable plate, wherein the movable plate is arranged inside the cylinder and is located on the right of the piston, the movable plate is able to reciprocate left and right in the cylinder, a vent hole passes through an outer wall of the cylinder is provided, and the vent hole is located between the piston and the movable plate;

a spring, wherein the spring is arranged between the piston and the movable plate, an end of the spring is fixedly connected to the piston, and the other end of the spring is fixedly connected to the movable plate;

a box, arranged on an outer wall of the right side of the cylinder;

a piston rod, wherein an end of the piston rod is fixedly connected to a right end of the movable plate, and a through hole is arranged in a right side wall surface of the cylinder, and the other end of the piston rod extends through the through hole to an interior of the box;

a rack, wherein the rack is arranged inside the box, and an end of the rack is fixedly connected to an end of the piston rod away from the movable plate;

a guide rod, wherein a guide hole is arranged in the right wall surface of the box, and an end of the guide rod is fixedly connected to the other end of the rack, the other end of the guide rod extends through the guide hole to the outside of the box;

a gear, wherein the gear is arranged below the rack, the rack is engaged with the gear, and a part of a curved surface of the gear is not toothed;

a rotating shaft, wherein the rotating shaft passes through a center of the gear, two ends of the rotating shaft are mounted on two side wall surfaces of the box through bearings, and the rotating shaft is perpendicular to the rack;

a grooved body, arranged on an outer wall of the box; and a motor, wherein the motor is fixed to an inner wall of the box, and an end of the rotating shaft extends to an interior of the box and is fixedly connected to an output shaft of the motor.

Preferably, the airbag vibration device further includes:

a limiting plate, wherein the limiting plate is arranged at an end of the guide rod extending out of the outer wall of the box, the limiting plate is circular, and the diameter of the limiting plate is larger than the diameter of the guide hole.

Preferably, the airbag vibration device further includes:

a switch arranged on an outer wall of the grooved body and electrically connected to the motor.

Preferably, the temperature sensor 23 and the controller 24 are connected by a temperature monitoring circuit and the temperature monitoring circuit includes:

an operational amplifier U1, wherein an inverting terminal of the operational amplifier U1 is connected to an end of a resistor R1, the other end of the resistor R1 is connected to an end of the temperature sensor 23, the other end of the temperature sensor 23 is connected to a +12V power supply, and an inductor L1 is connected in parallel with two ends of the resistor R1;

a non-inverting terminal of the operational amplifier U1 is connected to an end of a resistor R4, the other end of the resistor R4 is connected to a collector of a first transistor VT1, and a base of the first transistor VT1 is connected to an end of a resistor R3, the other end of the resistor R3 is respectively connected to an end of a resistor R2 and a cathode of a Zener diode D1, an anode of the Zener diode D1 is grounded, the other end of the resistor R2 is connected between the temperature sensor 23 and the resistor R1, and the resistor R3 is connected in parallel with a capacitor C1;

a signal output end of the operational amplifier U1 is connected to an end of a resistor R9, the other end of the resistor R9 is connected to an inverting terminal of the operational amplifier U2, and the resistor R9 is connected in parallel with a capacitor C3;

a non-inverting terminal of the operational amplifier U2 is connected to an end of a relay K, and the other end of the relay K is connected to a collector of a second transistor VT2, a first diode VD1 is connected in parallel with two ends of the relay K, a base of the second transistor VT2 is respectively connected to an end of a resistor R5 and an end of a resistor R6, the other end of the resistor R5 is connected to an emitter of the first transistor VT1, a second diode VD2 is connected in parallel with two ends of the resistor R5, the other end of the resistor R6 is connected to a cathode of the Zener diode D2, and an anode of the Zener diode D2 is grounded;

a signal output end of the operational amplifier U2 is connected to an end of a resistor R8, and the other end of the resistor R8 is connected to the non-inverting terminal of the operational amplifier U2, a capacitor C2 is connected in parallel with two ends of the resistor R8, the signal output end of the operational amplifier U2 is connected to an end of the resistor R7, the other end of a resistor R7 is connected to an emitter of the second transistor VT2, and an inductor L2 is connected in parallel with two ends of the resistor R7.

The technical solutions of the present disclosure have the following advantages. The thermostatic massage pad of the present disclosure includes: a thermostatic pad, wherein a thermostatic water pipe is arranged in the thermostatic pad. A cooling pad, wherein a cooling water pipe is arranged in the cooling pad. A casing, wherein a thermostatic water pump and a cooling water pump are respectively arranged inside the casing. A thermostatic water tank is arranged at the top of the thermostatic water pump, a cooling water tank is arranged at the top of the cooling water pump, the water inlet end of the thermostatic water pump is connected to the water outlet of the thermostatic water tank, and the water inlet end of the cooling water pump is connected to the water outlet of the cooling water tank. A thermoelectric cooler, wherein an end surface of the thermoelectric cooler is fixedly connected to the wall surface of the thermostatic water tank, the other end surface of the thermoelectric cooler is fixedly connected to the wall surface of the cooling water tank. A thermostatic connecting water pipe, wherein an end of the thermostatic connecting water pipe is connected to a water outlet end of the thermostatic water pump, the other end of the thermostatic connecting water pipe is connected to an end of the thermostatic water pipe, and the other end of the thermostatic water pipe is connected to a water inlet of the thermostatic water tank. A cooling connecting water pipe, wherein an end of the cooling connecting water pipe is connected to a water outlet end of the cooling water pump, the other end of the cooling connecting water pipe is connected to an end of the cooling water pipe, and the other end of the cooling water pipe is connected to the water inlet of the cooling water tank. Aa controller, wherein the controller is arranged on the inner wall of the casing, and the controller is electrically connected to the thermoelectric cooler. A power supply, wherein the power supply is arranged on the inner wall of the casing and is electrically connected to the thermoelectric cooler, the thermostatic water pump, and the cooling water pump, respectively. The temperature adjustment (heating or cooling) of the thermostatic pad is realized by controlling the current direction of the thermoelectric cooler by the controller. Meanwhile, the cooling pad functions to exchange heat with the outside, thereby realizing the heating or cooling of the contact area between the body of a patient having challenges in moving his/her body and the mattress etc., and improving the comfort of lying on a bed, so as to avoid the development of ulceration. Since the thermostatic water pipe is arranged inside the thermostatic pad, thermostatic pad made of cotton cloth would not affect the patient's comfort. The cooling pad is placed at a well-ventilated place in a room, which facilitates rapid heat exchange and improves the heat exchange efficiency. The thermostatic water tank, cooling water tank, thermostatic water pump, cooling water pump, controller, and power supply are all integrated in the box, which is lighter and easy to carry.

Other features and advantages of the present disclosure will be set forth in the description below. Some of these features and advantages will become apparent with the illustration of the description and some advantages can be understood by implementing the present disclosure. The objectives and other advantages of the present disclosure may be realized and obtained by means of the structures specified in the specification, claims, and drawings.

The technical solution of the present disclosure will be further described in detail below through the drawings and embodiments.

BRIEF DESCRIPTION OF THE DRAWINGS

The drawings which are intended to facilitate a further understanding of the present disclosure and to be considered as a part of the specification are used to explain the present disclosure together with the embodiments of the present disclosure rather than limit the present disclosure. In the drawings.

The reference numerals in the drawings are described below: 1—thermostatic pad, 2—thermostatic water pipe, 3—thermostatic connecting water pipe, 4—thermostatic water tank, 5—cooling water tank, 6—heating plate, 7—thermoelectric cooler, 8—cooling connecting water pipe, 9—cooling fan, 10—cooling water pipe, 11—cooling pad, 12—airbag, 13—massage pad, 14—air pipe, 15—inflation solenoid valve, 16—compressed air multi-way connector, 17—deflation solenoid valve, 18—air pump, 19—controller, 20—power supply, 21—thermostatic water pump, 22—cooling water pump, 23—temperature sensor, 24—control panel, 25—cylinder, 26—connecting pipe, 27—piston, 28—movable plate, 29—spring, 30—box, 31—piston rod, 32—through hole, 33—guide rod, 34—guide hole, 35—gear, 36—rotating shaft, 37—bearing, 38—grooved body, 39—motor, 40—limiting plate, 41—switch, 42—rack, 43—vent hole, 100—casing, 200—water pipe network module, 201—first water inlet pipe, 202—first curved water pipe, 203—S-shaped water pipe, 204—second curved water pipe, 205—first water outlet pipe, 140—water-cooled radiator, 141—water-cooled radiator housing; 1411—connecting plate; 1412—accommodating chamber; 1413—water collecting area; 1414—water-cooled radiator water inlet; 1415—water-cooled radiator water outlet; 142—heat exchange module; 143—second water inlet pipe; 144—second water outlet pipe; 1441—water outlet side hole.

DETAILED DESCRIPTION OF THE EMBODIMENTS

The preferred embodiments of the present disclosure are described below with reference to the drawings. It should be understood that the preferred embodiments described herein are only used to illustrate and explain the present disclosure rather than limit the present disclosure.

Figure 1:
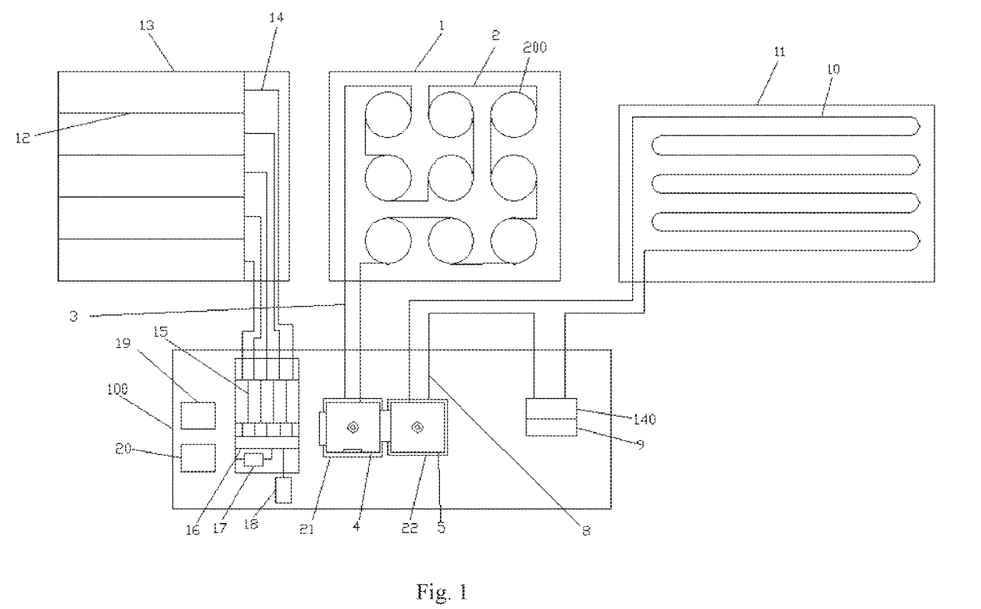
FIG. 1 is a structural schematic view of the present disclosure.
Figure 2:
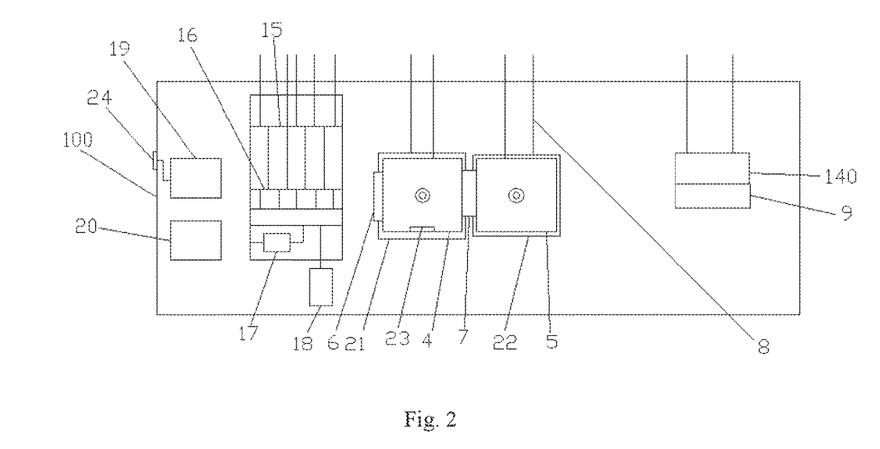
FIG. 2 is a schematic view showing the internal structure of a casing of the present disclosure.

According to an embodiment of the present disclosure, a thermostatic massage pad, as shown in FIGS. 1-2, includes:

the thermostatic pad 1, wherein the thermostatic water pipe 2 is arranged inside the thermostatic pad 1;

the cooling pad 11, wherein the cooling water pipe 10 is arranged inside the cooling pad 11;

the casing 100, wherein the thermostatic water pump 21 and the cooling water pump 22 are respectively arranged inside the casing 100, the thermostatic water tank 4 is arranged at the top of the thermostatic water pump 21, the cooling water tank 5 is arranged at the top of the cooling water pump 22, the water inlet end of the thermostatic water pump 21 is connected to the water outlet of the thermostatic water tank 4, and the water inlet end of the cooling water pump 22 is connected to the water outlet of the cooling water tank 5;

the thermoelectric cooler 7, wherein an end surface of the thermoelectric cooler 7 is fixedly connected to the wall surface of the thermostatic water tank 4, the other end surface of the thermoelectric cooler 7 is fixedly connected to the wall surface of the cooling water tank 5; the thermoelectric cooler is a heat pump having the advantage of no sliding parts and applicable in occasions with limited space, high reliability requirement, and without refrigerant contamination. According to the Peltier effect of the semiconductor material, when the direct current passes through a galvanic couple formed by serially connecting two dissimilar semiconductor materials, the heat absorption and heat emission can take place at two ends of the galvanic couple, thereby realizing the purpose of cooling. This is a refrigeration technology that produces negative thermal conductivity, which is characterized by having no moving parts and has high reliability. The model of the thermoelectric cooler is TEC2-19003;

the thermostatic connecting water pipe 3, wherein an end of the thermostatic connecting water pipe 3 is connected to a water outlet end of the thermostatic water pump 21, the other end of the thermostatic connecting water pipe 3 is connected to an end of the thermostatic water pipe 2, and the other end of the thermostatic water pipe 2 is connected to a water inlet of the thermostatic water tank 4;

the cooling connecting water pipe 8, wherein an end of the cooling connecting water pipe 8 is connected to a water outlet end of the cooling water pump 22, the other end of the cooling connecting water pipe 8 is connected to an end of the cooling water pipe 10, and the other end of the cooling water pipe 10 is connected to the water inlet of the cooling water tank 5;

the controller 19, wherein the controller 19 is arranged on the inner wall of the casing 100, and the controller 19 is electrically connected to the thermoelectric cooler 7 respectively. The model of the controller is MCU ATmega328; and the power supply 20, wherein the power supply 20 is arranged on the inner wall of the casing 100 and is electrically connected to the thermoelectric cooler 7, the thermostatic water pump 21, and the cooling water pump 22, respectively, the power supply uses a standard 20V or 12V power supply to provide electricity to the various parts inside the casing.

The working principle of the above technical solution is as follows. Place the thermostatic pad 1 on the bed. Let the paralyzed patient lie on the thermostatic pad 1, and place the cooling pad 11 at a well-ventilated place. When cooling the contact area of the skin, the controller 19 applies an electrical current to the thermoelectric cooler 7 and the end of the thermostatic water tank 4 in contact with the thermoelectric cooler 7 is cooled, so as to lower the water temperature in the thermostatic water tank 4. Driven by the thermostatic water pump 21, the cooled water successively flows through the thermostatic connecting water pipe 3, the thermostatic water pipe 2 and then flows back into the thermostatic water tank 4. The cooled water can lower the temperature of the thermostatic pad 1, thereby cooling the contact area between the patients' body and the thermostatic pad 1. While the end of the cooling water tank 5 is in contact with the thermoelectric cooler 7, the water is heated up, so that the water temperature in the cooling water tank 5 is increased. Driven by the cooling water pump 22, the heated water successively passes through the cooling water pipe 8 and the cooling water pipe 10 and then flows back into the cooling water tank 5. The heated water causes the rise of the temperature in the cooling pad 11, and the heat is dissipated into the air through the cooling pad 11. When the temperature of the thermostatic pad 11, at the area in contact with the body skin, raises the controller 19 applies a reverse electrical current to the thermoelectric cooler 7, and an end of the thermostatic water tank 4 in contact with the thermoelectric cooler 7 is heated and an end of the cooling water tank 5 in contact with the thermoelectric cooler 7 is cooled down, so that the thermostatic pad 1 is heated up, and the cooling pad 11 absorbs heat from the outside air.

The above technical solution has the following advantages. The temperature adjustment of the thermostatic pad 1 is realized by controlling the direction of the electrical current flowing through the thermoelectric cooler 7 by the controller 19. Meanwhile, the cooling pad 11 functions to exchange heat with the outside, thereby realizing the heating and cooling of the contact area between the body of a patient having challenges in moving his/her body and the mattress etc., achieving better heat dissipation and faster temperature control, improving the comfort of the patient lying on the bed, and avoiding the development of ulceration. Since the thermostatic water pipe 2 is arranged inside the thermostatic pad 1, the thermostatic pad 1 made of cotton cloth would not affect the patient's comfort. The cooling pad is placed at a well-ventilated place in the room, which facilitates rapid heat exchange and improves the heat exchange efficiency. The thermostatic water tank 4, the cooling water tank 5, the thermostatic water pump 21, the cooling water pump 22, the controller 19, and the power supply 20 are all integrated in the box 100, which is lighter and easy to carry.

In one embodiment, as shown in FIGS. 1-2, the thermostatic massage pad further includes a massage device. The massage device includes:

the massage pad 13, wherein a plurality of independent airbags 12 are arranged inside the massage pad 13;

the inflation solenoid valves 15, wherein the inflation solenoid valves 15 are arranged inside the casing 100, and the inflation solenoid valves 15 are electrically connected to the controller 19;

a plurality of air pipes 14, wherein the air pipes 14 are connected to the airbags 12 at an end, and the air pipes 14 are connected to the outlet ends of the inflation solenoid valves 15 at the other end;

the compressed air multi-way connector 16, wherein the compressed air multi-way connector 16 is arranged inside the casing 100, and a plurality of output ends of the compressed air multi-way connector 16 are respectively connected to the inlet ends of the inflation solenoid valves 15;

the deflation solenoid valve 17, wherein the deflation solenoid valve 17 is arranged inside the casing 100, an inlet of the deflation solenoid valve 17 is connected to the air discharge end of the compressed air multi-way connector 16, an outlet of the deflation solenoid valve 17 is connected to the outside, and the deflation solenoid valve 17 is electrically connected to the controller 19; and the air pump 18, wherein the air pump 18 is arranged inside the casing 100, and an output end of the air pump 18 is connected to the air inlet end of the compressed air multi-way connector 16.

The working principle of the above technical solution is as follows. When the patient needs a massage on the skin, place the massage pad 13 on the bed. Let the patient lie on the massage pad 13, and then start up the air pump 18, so that the compressed air would enter through the compressed air multi-way connector 16. After the inflation solenoid valves 15 are successively opened by the controller 19, the compressed air successively enters the airbags 12 through the respective air pipes 14. Then, the deflation solenoid valve 17 is opened by the controller 19, so as to open the air discharging end of the compressed air multi-way connector 16 to release the compressed air and evacuate the airbags, successively. Therefore, the airbags can be inflated and deflated successively and the various parts of the skin getting the massage, successively.

The above technical solution has the following advantages. Since the contact area between the skin and the massage pad undergoes a constant impact with the contraction or expansion of the airbag, the blood circulation can be promoted, the metabolism can be accelerated, and the development of necrosis or ulceration of the skin tissues is reduced. In addition, as the massage is performed by inflating or deflating the airbags, the massage is performed in a softer way and the extra damage on the affected skin is reduced.

In one embodiment, as shown in FIG. 2, the heating plate 6 is arranged on the wall surface of the thermostatic water tank 4 and the heating plate 6 is electrically connected to the controller 19.

The above technical solution has the following advantages. When it is not required to rapidly raise the temperature, the heating plate 6 can be activated by the controller 19, so as to raise the water temperature in the thermostatic water tank 4, thereby achieving the heating effect. In the cold weather, the cooling pad, the cooling water circulation, and the thermoelectric cooler may also be removed to make the structure lighter and simpler.

In one embodiment, the thermostatic massage pad further includes:

the temperature sensor 23, wherein the temperature sensor 23 is arranged on the inner wall of the thermostatic water tank 4, the temperature sensor 23 is electrically connected to the controller 19. The model of the temperature sensor 23 is PT100; and the control panel 24, wherein the control panel 24 is arranged on the outer wall of the casing 100, and the control panel 24 is electrically connected to the controller 19.

The above technical solution has the following advantages. The temperature sensor 23 is used to monitor the water temperature in the thermostatic water tank 4, and the value of the water temperature can be set on the control panel 24. The direction of the electrical current flowing through the thermoelectric cooler 7 is controlled by the controller 19 to realize the heating or cooling of the water in the thermostatic water tank 4, and the heating or cooling of the water is monitored by the temperature sensor 23 to give feedback to the controller 19. After comparison with the set temperature value, the current of the thermoelectric cooler is controlled according to the comparison value, so that the water temperature in the thermostatic water tank 4 is always maintained at a constant value, thereby providing a more suitable and comfortable temperature at the contact area between the patients' skin and the mattress.

Figure 3:
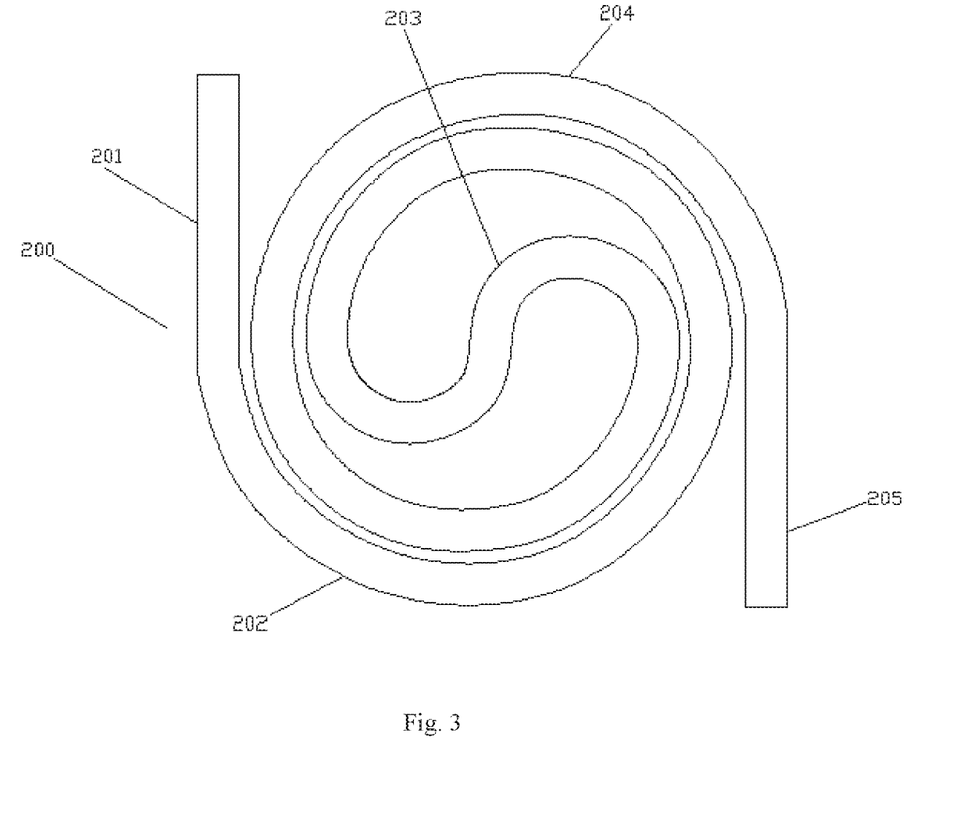
FIG. 3 is a structural schematic view of a water pipe network module of the present disclosure.

In one embodiment, as shown in FIG. 3, the thermostatic water pipe 2 includes a plurality of water pipe network modules 200 and the plurality of water pipe network modules 200 are arranged inside the thermostatic pad 1 in a rectangular array manner. Each water pipe network module 200 includes:

the first water inlet pipe 201;

the first curved water pipe 202, wherein the first curved water pipe 202 is curved along a counterclockwise direction, and the inlet end of the first curved water pipe 202 is connected to the outlet end of the first water inlet pipe 201;

the S-shaped water pipe 203, wherein the inlet end of the S-shaped water pipe 203 is connected to the outlet end of the first curved water pipe 202;

the second curved water pipe 204, wherein the second curved water pipe 204 is curved along a clockwise direction opposite to the first curved water pipe, the inlet end of the second curved water pipe 204 is connected to the outlet end of the S-shaped water pipe 203, and the second curved water pipe 204 is of an arc shape:

the first water outlet pipe 205, wherein the inlet end of the first water outlet pipe 205 is connected to the outlet end of the second curved water pipe 204;

the plurality of water pipe network modules 200 are successively connected end to end, and the inlet end of the first water inlet pipe 201 of the first network module 200 is connected to an end of the thermostatic connecting water pipe 3 away from the thermostatic water pump 21, the outlet end of the first water outlet pipe 205 of the last water pipe network module 200 is connected to the water inlet of the thermostatic water tank 4.

The above technical solution has the following advantages. The water from the thermostatic water tank 4 is circulated in the plurality of water pipe network modules 200 and the water flow passes through the first water inlet pipe 201, the first curved water pipe 202, the S-shaped water pipe 203, the second curved water pipe 204, and the first water outlet pipe 205 in sequence, so that the contact area between the water and the thermostatic pad 1 is increased with the pipes, which greatly improves the heat exchange efficiency and speeds up the heating or cooling of the thermostatic pad 1.

Figure 8:
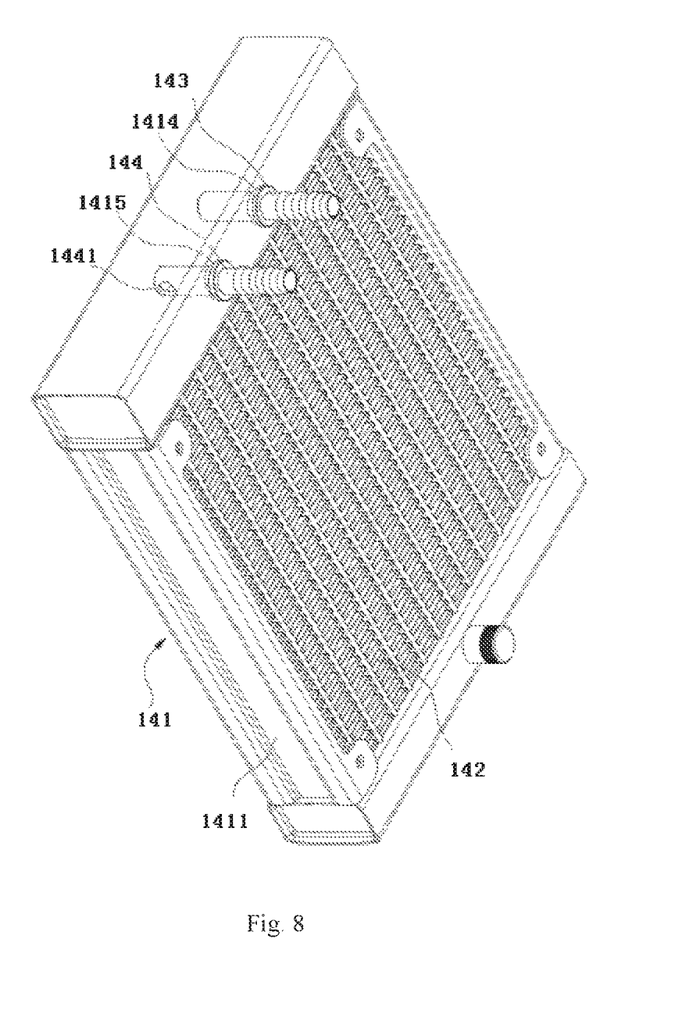
FIG. 8 is a structural schematic view of a water-cooled radiator of the present disclosure.
Figure 9:
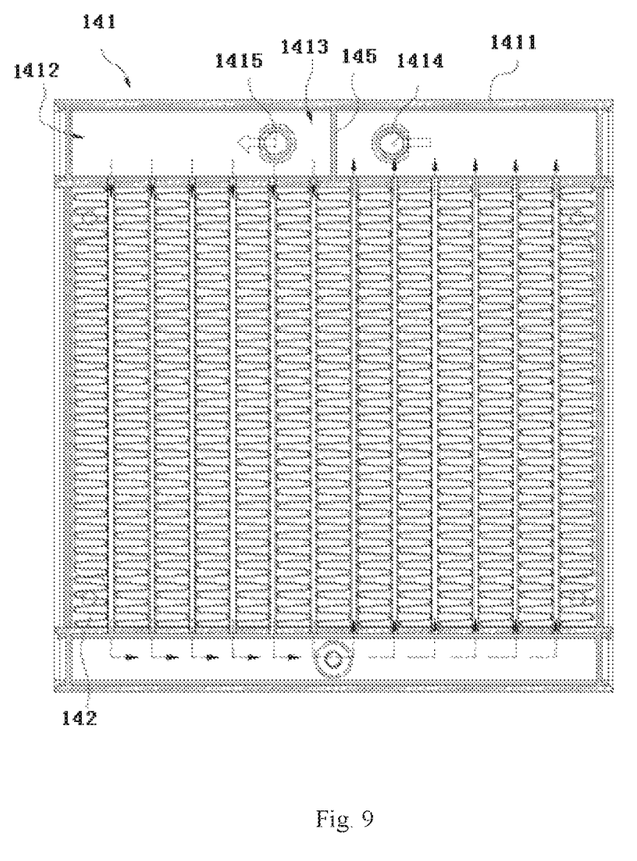
FIG. 9 is a sectional view of the water-cooled radiator of the present disclosure.

In one embodiment, as shown in FIGS. 8-9, the cooling fan 9 and the water-cooled radiator 140 are installed on the cooling connecting water pipe 8. The cooling fan 9 is arranged in parallel with the water-cooled radiator 140, and the cooling fan 9 is electrically connected to the controller 19. The cooling fan 9 is controlled by the controller 19, and the cooling fan 9 forces air onto and cools the water-cooled radiator 140. The water-cooled radiator increases the heat dissipation area and the cooling fan speeds up the heat dissipation.

The water-cooled radiator 140 includes:

the water-cooled radiator housing 141, wherein the water-cooled radiator housing 141 includes the plurality of connecting plates 1411, the plurality of the connecting plates 1411 make an accommodating chamber 1412, the water-cooled radiator housing 141 has the water collecting area 1413 on the side of the accommodating chamber 1412, one of the connecting plates 1411 is provided with the water-cooled radiator water inlet 1414 and the water-cooled radiator water outlet 1415, the water-cooled radiator water inlet 1414 and the water-cooled radiator water outlet 1415 are arranged in the water collecting area 1413, and the water-cooled radiator water inlet 1414 and the water-cooled radiator water outlet 1415 are both connected to the accommodating chamber 1412;

the heat exchange module 142, wherein the heat exchange module 142 is arranged inside the accommodating chamber 1412, and the heat exchange module 142 includes a plurality of wavy cooling fins;

the second water inlet pipe 143, wherein the second water inlet pipe 143 is inserted in the water-cooled radiator water inlet 1414, an end of the second water inlet pipe 143 is exposed outside the water-cooled radiator housing 141 and is connected to the inlet end of the cooling connecting water pipe 8, the other end of the second water inlet pipe 143 extends from the water-cooled radiator water inlet 1414 to the accommodating chamber 1412:

the second water outlet pipe 144, wherein the second water outlet pipe 144 is inserted in the water-cooled radiator water outlet 1415, an end of the second water outlet pipe 144 is exposed outside the water-cooled radiator housing 141 and is connected to the outlet end of the cooling connecting water pipe 8, the other end of the second water outlet pipe 144 extends from the water-cooled radiator water outlet 1415 to the accommodating chamber 1412, the second water outlet pipe 144 is provided with the water outlet side hole 1441 at the end extending into the accommodating chamber 1412, and in the water-cooled radiator structure, the water outlet side hole 1441 is covered by the water in the accommodating chamber 1412 to prevent air from entering the second water outlet pipe 144; and the partition plate, wherein the partition plate is arranged inside the accommodating chamber 1412 and is located between the second water inlet pipe 143 and the second water outlet pipe 144, and the partition plate connects the two opposite inner wall surfaces of the accommodating chamber 1412.

The above technical solution has the following advantages. In the above structure, the water collecting area 1413 is formed with the water inlet pipe 143, so that the water in the water collecting area 1413 can flow from the water inlet pipe 143 into the heat exchange area. With such a configuration, the water-cooled radiator can be arranged at different angles and directions without affecting the transportation of the water to the heat exchange area and the water in the water collecting area 1413 only needs to cover the water outlet side hole 1441 on the water outlet pipe 144 to prevent air from entering the water outlet pipe 144. Namely, the air is prevented from being sucked into the water pump, so as to maintain normal operation of the water pump.

Figure 4:
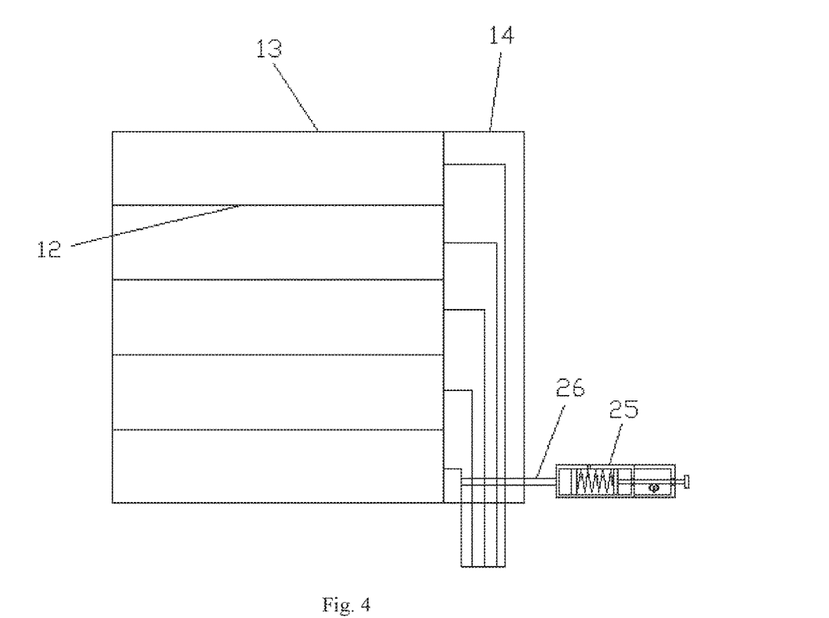
FIG. 4 is an installation diagram of an airbag vibration device of the present disclosure.
Figure 5:
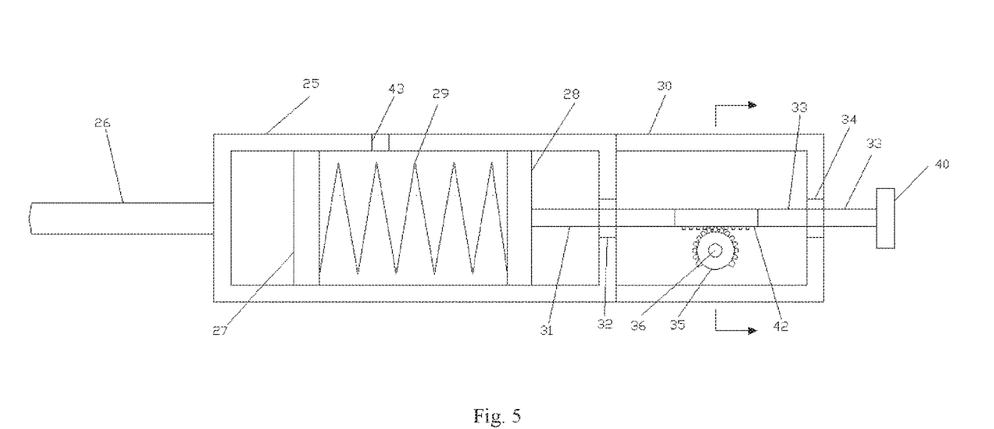
FIG. 5 is a structural schematic view of the airbag vibration device of the present disclosure.
Figure 6:
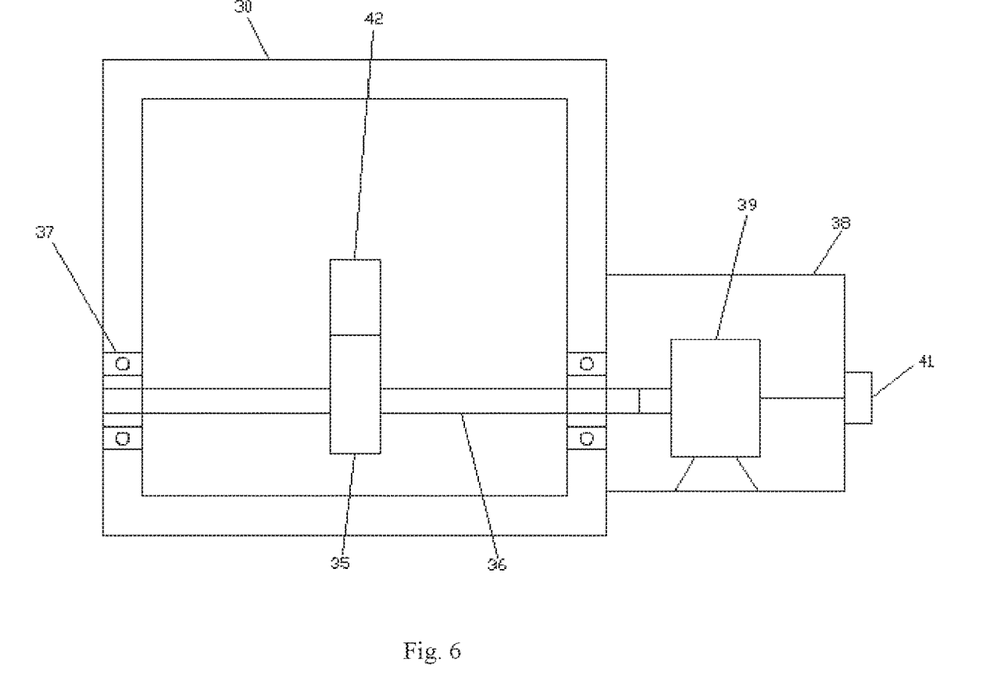
FIG. 6 is a sectional view of section A-A of the present disclosure.

In one embodiment, as shown in FIGS. 4-6, the air pipes 14 are further provided with an airbag vibration device. The airbag vibration device includes:

the cylinder 25, arranged at a place near the air pipes 14;

the connecting pipe 26, wherein an end of the connecting pipe 26 is connected to the air pipes 14, and the other end of the connecting pipe 26 is connected to the left end of the cylinder 25;

the piston 27, wherein the piston 27 is arranged inside the cylinder 25, and the piston 27 reciprocates left and right within the cylinder 25;

the movable plate 28, wherein the movable plate 28 is arranged inside the cylinder 25 and is located on the right of the piston 27, the movable plate 28 can reciprocate left and right in the cylinder 25, the vent hole 43 is arranged in an outer wall of the cylinder 25, and the vent hole 43 is located between the piston 27 and the movable plate 28;

the spring 29, wherein the spring 29 is arranged between the piston 27 and the movable plate 28, an end of the spring 29 is fixedly connected to the piston 27, and the other end of the spring 29 is fixedly connected to the movable plate 28;

the box 30, arranged on an outer wall on the right side of the cylinder 25;

the piston rod 31, wherein an end of the piston rod 31 is fixedly connected to the right end of the movable plate 28, the through hole 32 is arranged in the right wall surface of the cylinder 25, and the other end of the piston rod 31 extends through the through hole 32 to the inside of the box 30;

the rack 42, wherein the rack 42 is arranged inside the box 30, and an end of the rack 42 is fixedly connected to an end of the piston rod 31 away from the movable plate 28;

the guide rod 33, wherein the guide hole 34 is arranged in the right wall surface of the box 30, an end of the guide rod 33 is fixedly connected with the other end of the rack 42, and the other end of the guide rod 33 extends through the guide hole 34 to the outside of the box 30;

the gear 35, wherein the gear 35 is arranged below the rack 42, the rack 42 is engaged with the gear 35, and a part of the curved surface of the gear 35 is not toothed;

the rotating shaft 36, wherein the rotating shaft 36 passes through the center of the gear 35, two ends of the rotating shaft 36 are mounted on two side walls of the box 30 through bearings 37, and the rotating shaft 36 is perpendicular to the rack 42;

the grooved body 38, arranged on the outer wall of the box 30; and the motor 39, wherein the motor 39 is fixed on the inner wall of the box 30, and an end of the rotating shaft 36 extends to the inside of the box 30 and is fixedly connected to the output shaft of the motor 39.

The working principle of the above technical solution is as follows. The motor 39 drives the rotating shaft 36 to rotate. The rotating shaft 36 drives the gear 35 to rotate and the rack 42 moves left and right with the engagement of the gear 35 and the rack 42. The rack 42 further drives the piston rod 31 to move to the right in the through hole 32 and the guide rod 33 moves to the right in the guide hole 34. When the gear 35 is turned to the gearless part, since the gear 35 and the rack 42 cannot be engaged, the movable plate 28 moves to the left with the elastic force of the spring 29.

When the gear 35 engages with the rack 42 again, the movable plate 28 can be driven to move to the left again, thereby realizing the left and right reciprocating movement of the movable plate 28. When the movable plate 28 moves, the piston 27 follows the movement, resulting in the constant change of the relative position between the piston 27 and the vent hole 43. The left end of the piston 27 is connected to the air pipes 14 through the connecting pipe 26 and is subjected to the pressure from the airbag 12. When the air pressure is greater than the balancing pressure of the spring, the piston 27 will be pushed to the right side of the vent hole 43 to release pressure until the balanced pressure is restored. Since the position of the piston 27 moves left and right, the balancing pressure between the air pressure and the spring constantly changes, and as a result, the pressure inside the airbag 12 is constantly changed to produce a massage effect.

The above technical solution has the following advantages. The piston 27 moves left and right due to the movement of the gear 35 and the rack 42 with intermittent engagement, thereby constantly changing the balance between the spring 29 and the air pressure. As a result, the pressure inside the airbag 12 is constantly changed, so the size of the airbag is changed and the variation range of the airbag size is wider. Therefore, the expansion or contraction is smoother and the massage to the affected skin by the airbag is more comfortable. Moreover, the adjustment of the massage frequency can also be achieved by adjusting the rotation speed of the motor, which makes the frequency adjustment of the massage and vibration of the airbag more convenient.

In one embodiment, as shown in FIG. 5, the airbag vibration device further includes: the limiting plate 40, wherein the limiting plate 40 is arranged at an end of the guide rod 33 extending out of the outer wall of the box 30. The limiting plate 40 is circular and the diameter of the limiting plate 40 is larger than the diameter of the guide hole 34.

The above technical solution has the following advantages. The limiting plate 40 functions to limit the displacement of the guide rod 33 and prevents the guide rod 33 from moving beyond the limit. Also, the guide rod 33 plays the role of supporting the rack 42, so as to make the left and right movement of the rack 42 steadier.

In one embodiment, as shown in FIG. 6, the airbag vibration device further includes: the switch 41, wherein the switch 41 is arranged on the outer wall of the grooved body 38 and the switch 41 is electrically connected to the motor 39.

The above technical solution has the following advantage. The switch is used to control the on or off of the motor 39.

Figure 7:
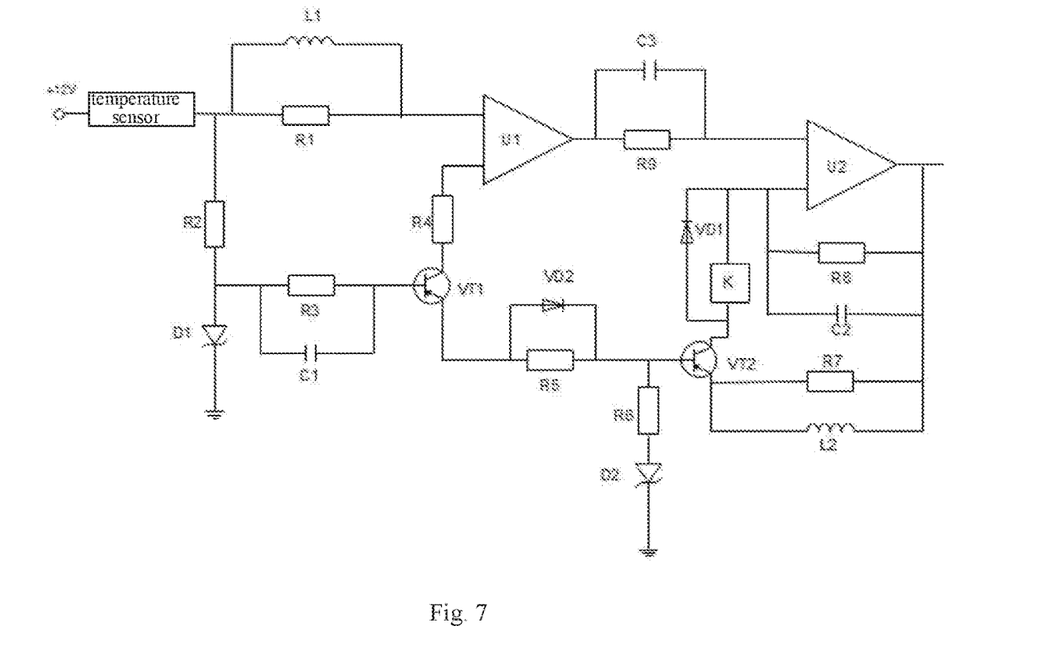
FIG. 7 is a structural schematic view of a temperature monitoring circuit of the present disclosure.

In one embodiment, as shown in FIG. 7, the temperature sensor 23 and the controller 24 are connected by a temperature monitoring circuit, and the temperature monitoring circuit includes:

the operational amplifier U1, wherein the inverting terminal of the operational amplifier U1 is connected to an end of the resistor R1, the other end of the resistor R1 is connected to an end of the temperature sensor 23, the other end of the temperature sensor 23 is connected to a +12V power supply, and the inductor L1 is connected in parallel with the resistor R1 at two ends;

a non-inverting terminal of the operational amplifier U1 is connected to an end of the resistor R4, the other end of the resistor R4 is connected to a collector of the first transistor VT1, and a base of the first transistor VT1 is connected to an end of the resistor R3, the other end of the resistor R3 is respectively connected to an end of the resistor R2 and a cathode of the Zener diode D1, an anode of the Zener diode D1 is grounded, the other end of the resistor R2 is connected between the temperature sensor 23 and the resistor R1, and the resistor R3 is connected in parallel with the capacitor C1;

a signal output end of the operational amplifier U1 is connected to an end of the resistor R9, the other end of the resistor R9 is connected to an inverting terminal of the operational amplifier U2, and the resistor R9 is connected in parallel with the capacitor C3;

a non-inverting terminal of the operational amplifier U2 is connected to an end of the relay K, and the other end of the relay K is connected to a collector of the second transistor VT2, the first diode VD1 is connected in parallel with two ends of the relay K, a base of the second transistor VT2 is respectively connected to an end of the resistor R5 and an end of the resistor R6, the other end of the resistor R5 is connected to an emitter of the first transistor VT1, the second diode VD2 is connected in parallel with two ends of the resistor R5, the other end of the resistor R6 is connected to a cathode of the Zener diode D2, and an anode of the Zener diode D2 is grounded;

a signal output end of the operational amplifier U2 is connected to an end of the resistor R8, and the other end of the resistor R8 is connected to the non-inverting terminal of the operational amplifier U2, the capacitor C2 is connected in parallel with two ends of the resistor R8, the signal output end of the operational amplifier U2 is connected to an end of the resistor R7, the other end of the resistor R7 is connected to an emitter of the second transistor VT2, and the inductor L2 is connected in parallel with two ends of the resistor R7.

The above technical solution has the following advantages. The temperature monitoring circuit can monitor the water temperature in the thermostatic water tank 4 to keep the water temperature constant. Such a circuit has a simple structure, stable performance, and is convenient in installation and debugging.

Obviously, various modifications and variations may be made by those skilled in the art without departing from the spirit and scope of the present disclosure. Therefore, if such modifications and variations of the present disclosure fall within the scope of the appended claims and the equivalent technique thereof, then the present disclosure is also intended to include such modifications and variations.

What is claimed is:

1. A thermostatic massage pad, comprising:
a thermostatic pad, wherein a thermostatic water pipe is arranged inside the thermostatic pad;
a cooling pad, wherein a cooling water pipe is arranged inside the cooling pad;
a casing, wherein a thermostatic water pump and a cooling water pump are respectively arranged inside the casing, a thermostatic water tank is arranged at a top of the thermostatic water pump, a cooling water tank is arranged at a top of the cooling water pump, a water inlet end of the thermostatic water pump is connected to a water outlet of the thermostatic water tank, and a water inlet end of the cooling water pump is connected to a water outlet of the cooling water tank;
a thermoelectric cooler, wherein a first end surface of the thermoelectric cooler is fixedly connected to a wall surface of the thermostatic water tank, a second end surface of the thermoelectric cooler is fixedly connected to a wall surface of the cooling water tank;
a thermostatic connecting water pipe, wherein a first end of the thermostatic connecting water pipe is connected to a water outlet end of the thermostatic water pump, a second end of the thermostatic connecting water pipe is connected to a first end of the thermostatic water pipe, and a second end of the thermostatic water pipe is connected to a water inlet of the thermostatic water tank;

a cooling connecting water pipe, wherein a first end of the cooling connecting water pipe is connected to a water outlet end of the cooling water pump, a second end of the cooling connecting water pipe is connected to a first end of the cooling water pipe, and a second end of the cooling water pipe is connected to a water inlet of the cooling water tank;

a controller, wherein the controller is arranged on an inner wall of the casing, and the controller is electrically connected to the thermoelectric cooler; and a power supply, wherein the power supply is arranged on the inner wall of the casing and is electrically connected to the thermoelectric cooler, the thermostatic water pump, and the cooling water pump, respectively.

2. The thermostatic massage pad according to claim 1, further comprising a massage device, wherein the massage device comprises:
a massage pad, wherein a plurality of independent airbags are arranged inside the massage pad;
a plurality of inflation solenoid valves, wherein the plurality of inflation solenoid valves are arranged inside the casing and are electrically connected to the controller;
a plurality of air pipes, wherein first ends of the plurality of air pipes are connected to the plurality of independent airbags, and second ends of the plurality of air pipes are connected to outlet ends of the plurality of inflation solenoid valves;
a compressed air multi-way connector, wherein the compressed air multi-way connector is arranged inside the casing, a plurality of output ends of the compressed air multi-way connector are respectively connected to a plurality of inlet ends of the plurality of inflation solenoid valves;
a deflation solenoid valve, wherein the deflation solenoid valve is arranged inside the casing, an inlet of the deflation solenoid valve is connected to an air discharge end of the compressed air multi-way connector, an outlet of the deflation solenoid valve is connected to an outside, and the deflation solenoid valve is electrically connected to the controller; and
an air pump, wherein the air pump is arranged inside the casing, and an output end of the air pump is connected to an air inlet end of the compressed air multi-way connector.

3. The thermostatic massage pad according to claim 1, wherein a heating plate is arranged on the wall surface of the thermostatic water tank, and the heating plate is electrically connected to the controller.

4. The thermostatic massage pad according to claim 1, further comprising:
a temperature sensor, wherein the temperature sensor is arranged on an inner wall of the thermostatic water tank, and the temperature sensor is electrically connected to the controller; and
a control panel, wherein the control panel is arranged on an outer wall of the casing, and the control panel is electrically connected to the controller.

5. The thermostatic massage pad according to claim 1, wherein the thermostatic water pipe comprises a plurality of water pipe network modules, and the plurality of water pipe network modules are arranged inside the thermostatic pad in a rectangular array manner, each of the plurality of water pipe network modules comprises:
a first water inlet pipe;
a first curved water pipe, wherein the first curved water pipe is curved along a counterclockwise direction, and an inlet end of the first curved water pipe is connected to an outlet end of the first water inlet pipe;
an S-shaped water pipe, wherein an inlet end of the S-shaped water pipe is connected to an outlet end of the first curved water pipe;
a second curved water pipe, wherein the second curved water pipe is curved along a clockwise direction opposite to the first curved water pipe, an inlet end of the second curved water pipe is connected to an outlet end of the S-shaped water pipe, and the second curved water pipe is of an arc shape; and
a first water outlet pipe, wherein an inlet end of the first water outlet pipe is connected to an outlet end of the second curved water pipe;
wherein, the plurality of water pipe network modules are successively connected end to end, and an inlet end of the first water inlet pipe of a first water pipe network module is connected to the second end of the thermostatic connecting water pipe away from the thermostatic water pump, and an outlet end of the first water outlet pipe of a last water pipe network module is connected to the water inlet of the thermostatic water tank.

6. The thermostatic massage pad according to claim 1, wherein a cooling fan and a water-cooled radiator are installed on the cooling connecting water pipe, the cooling fan is arranged in parallel with the water-cooled radiator, and the cooling fan is electrically connected to the controller;
the water-cooled radiator comprises:
a water-cooled radiator housing, wherein the water-cooled radiator housing comprises a plurality of connecting plates, the plurality of connecting plates make an accommodating chamber, the water-cooled radiator housing comprises a water collecting area on a side of the accommodating chamber, one of the plurality of connecting plates is provided with a water-cooled radiator water inlet and a water-cooled radiator water outlet, the water-cooled radiator water inlet and the water-cooled radiator water outlet are arranged in the water collecting area, and the water-cooled radiator water inlet and the water-cooled radiator water outlet are both connected to the accommodating chamber;
a heat exchange module, wherein the heat exchange module is arranged inside the accommodating chamber, and the heat exchange module comprises a plurality of wavy cooling fins;
a second water inlet pipe, wherein the second water inlet pipe is inserted in the water-cooled radiator water inlet, a first end of the second water inlet pipe is exposed outside the water-cooled radiator housing and is connected to an inlet of the cooling connecting water pipe, a second end of the second water inlet pipe extends from the water-cooled radiator water inlet to the accommodating chamber;
a second water outlet pipe, wherein the second water outlet pipe is inserted in the water-cooled radiator water outlet, a first end of the second water outlet pipe is exposed outside the water-cooled radiator housing and is connected to an output end of the cooling connecting water pipe, a second end of the second water outlet pipe extends from the water-cooled radiator water outlet to the accommodating chamber, the second water outlet pipe is provided with a water outlet side hole at an end extending into the accommodating chamber, and in a water-cooled radiator structure, the water outlet side hole is covered by water in the accommodating chamber to prevent air from entering the second water outlet pipe; and a partition plate, wherein the partition plate is arranged inside the accommodating chamber and is located between the second water inlet pipe and the second water outlet pipe, and the partition plate connects two opposite inner wall surfaces of the accommodating chamber.

7. The thermostatic massage pad according to claim 1, wherein a plurality of air pipes are further arranged with an airbag vibration device, and the airbag vibration device comprises:

a cylinder, arranged at a position beside the plurality of air pipes;

a connecting pipe, wherein a first end of the connecting pipe is connected to the plurality of air pipes, and a second end of the connecting pipe is connected to a left end of the cylinder;

a piston, wherein the piston is arranged inside the cylinder, and the piston reciprocates left and right within the cylinder;

a movable plate, wherein the movable plate is arranged inside the cylinder and is located on a right of the piston, the movable plate reciprocates left and right in the cylinder, a vent hole is arranged in an outer wall of the cylinder, and the vent hole is located between the piston and the movable plate;

a spring, wherein the spring is arranged between the piston and the movable plate, a first end of the spring is fixedly connected to the piston, and a second end of the spring is fixedly connected to the movable plate;

a box, arranged on a right side of the outer wall of the cylinder;

a piston rod, wherein a first end of the piston rod is fixedly connected to a right end of the movable plate, a through hole is arranged in a right wall surface of the cylinder, and a second end of the piston rod extends through the through hole to an inside of the box;

a rack, wherein the rack is arranged inside the box, and a first end of the rack is fixedly connected to the second end of the piston rod away from the movable plate;

a guide rod, wherein a guide hole is arranged in a right wall surface of the box, a first end of the guide rod is fixedly connected to a second end of the rack, and a second end of the guide rod extends through the guide hole to an outside of the box;

a gear, wherein the gear is arranged below the rack, the rack is engaged with the gear, and a part of a curved surface of the gear is not toothed;

a rotating shaft, wherein the rotating shaft passes through a center of the gear, two ends of the rotating shaft are mounted on two side walls of the box through bearings, and the rotating shaft is perpendicular to the rack;

a grooved body, arranged on an outer wall of the box; and a motor, wherein the motor is fixed to an inner wall of the box, and an end of the rotating shaft extends to the inside of the box and is fixedly connected to an output shaft of the motor.

8. The thermostatic massage pad according to claim 7, wherein the airbag vibration device further comprises:

a limiting plate, wherein the limiting plate is arranged at the second end of the guide rod extending out of the outer wall of the box, the limiting plate is circular, and a diameter of the limiting plate is larger than a diameter of the guide hole.

9. The thermostatic massage pad according to claim 7, wherein the airbag vibration device further comprises:

a switch, wherein the switch is arranged on an outer wall of the grooved body, and the switch is electrically connected to the motor.

10. The thermostatic massage pad according to claim 4, wherein the temperature sensor and the controller are connected by a temperature monitoring circuit, and the temperature monitoring circuit comprises:

a first operational amplifier, wherein an inverting terminal of the first operational amplifier is connected to a first end of a first resistor, a second end of the first resistor is connected to a first end of the temperature sensor, a second end of the temperature sensor is connected to a +12V power supply, and a first inductor is connected in parallel to the first end of the first resistor and the second end of the first resistor;

wherein, a non-inverting terminal of the first operational amplifier is connected to a first end of a second resistor, a second end of the second resistor is connected to a collector of a first transistor, and a base of the first transistor is connected to a first end of a third resistor, a second end of the third resistor is respectively connected to a first end of a fourth resistor and a cathode of a first Zener diode, an anode of the first Zener diode is grounded, a second end of the fourth resistor is connected between the temperature sensor and the first resistor, and the third resistor is connected in parallel with a first capacitor;

a signal output end of the first operational amplifier is connected to a first end of a fifth resistor, a second end of the fifth resistor is connected to an inverting terminal of a second operational amplifier, and the fifth resistor is connected in parallel with a second capacitor;

a non-inverting terminal of the second operational amplifier is connected to a first end of a relay, and a second end of the relay is connected to a collector of a second transistor, a first diode is connected in parallel to the first end of the relay and the second end of the relay, a base of the second transistor is respectively connected to a first end of a sixth resistor and a first end of a seventh resistor, a second end of the sixth resistor is connected to an emitter of the first transistor, a second diode is connected in parallel to the first end of the sixth resistor and the second end of the sixth resistor, a second end of the seventh resistor is connected to a cathode of a second Zener diode, and an anode of the second Zener diode is grounded;

a signal output end of the second operational amplifier is connected to a first end of an eighth resistor, and a second end of the eighth resistor is connected to the non-inverting terminal of the second operational amplifier, a third capacitor is connected in parallel to the first end of the eighth resistor and the second end of the eighth resistor, the signal output end of the second operational amplifier is connected to a first end of a ninth resistor, a second end of the ninth resistor is connected to an emitter of the second transistor, and a second inductor is connected in parallel to the first end of the ninth resistor and the second end of the ninth resistor.

* * * * *